United States Patent [19]
Enokida et al.

[11] Patent Number: 6,001,284
[45] Date of Patent: Dec. 14, 1999

[54] ORGANOELECTROLUMINESCENCE DEVICE MATERIAL AND ORGANOELECTROLUMINESCENCE DEVICE FOR WHICH THE MATERIAL IS ADAPTED

[75] Inventors: Toshio Enokida; Michiko Tamano; Satoshi Okutsu, all of Tokyo, Japan

[73] Assignee: Toyo Ink Manufacturing Co., Ltd., Tokyo, Japan

[21] Appl. No.: 08/688,876

[22] Filed: Jul. 31, 1996

[30] Foreign Application Priority Data

Aug. 4, 1995 [JP] Japan .................................. 7-199339

[51] Int. Cl.[6] .............................. G02F 1/00; B32B 9/00; C07F 15/00
[52] U.S. Cl. ........................ 252/583; 428/690; 428/917; 556/32
[58] Field of Search .................................. 252/700, 583, 252/301.16; 257/21; 428/917, 690; 534/15; 556/32

[56] References Cited

U.S. PATENT DOCUMENTS

| | | | |
|---|---|---|---|
| 5,294,869 | 3/1994 | Tang et al. ............................... | 313/504 |
| 5,405,709 | 4/1995 | Littman et al. ......................... | 428/690 |
| 5,456,988 | 10/1995 | Sano et al. .............................. | 428/690 |
| 5,712,051 | 1/1998 | Sugiura et al. ......................... | 428/690 |

FOREIGN PATENT DOCUMENTS 0 554 569    8/1993    European Pat. Off. .

OTHER PUBLICATIONS

Burrows et al., *Applied Physics Letters*, vol. 64, No. 20, May 16, (1994), pp. 2718–2720.
Sapochak et al., *Polym. Mater. Sci. Eng.* (1995) vol. 72, pp. 331–332.

*Primary Examiner*—Philip Tucker
*Attorney, Agent, or Firm*—Wenderoth, Lind & Ponack, L.L.P.

[57] ABSTRACT

An organic EL device which is excellent in stability in the repetitive operation and has a high light emission brightness can be obtained from a gallium complex of the general formula (1),

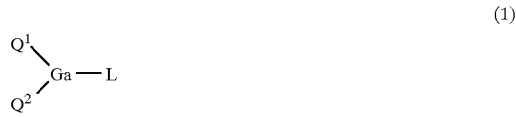

(1)

wherein each of $Q^1$ and $Q^2$ is independently a ligand of the general formula (2); and L is a halogen atom, a substituted or unsubstituted alkyl group, a substituted or unsubstituted cycloalkyl group, a substituted or unsubstituted aryl group, a substituted or unsubstituted heterocyclic ring group, $-OR^1$ in which $R^1$ is a hydrogen atom, a substituted or unsubstituted alkyl group, a substituted or unsubstituted cycloalkyl group, a substituted or unsubstituted aryl group or a substituted or unsubstituted heterocyclic ring group, or $-O-Ga-Q^3(Q^4)$ in which $Q^3$ and $Q^4$ have the same meanings as those of $Q^1$ and $Q^2$,

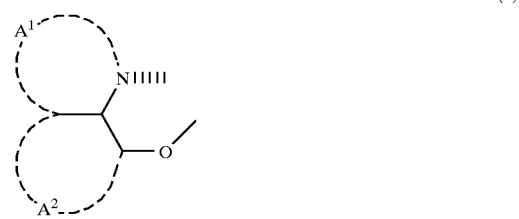

(2)

wherein $A^1$ and $A^2$ are substituted or unsubstituted six-membered aryl rings which are mutually fused to form a fused ring moiety.

10 Claims, 6 Drawing Sheets

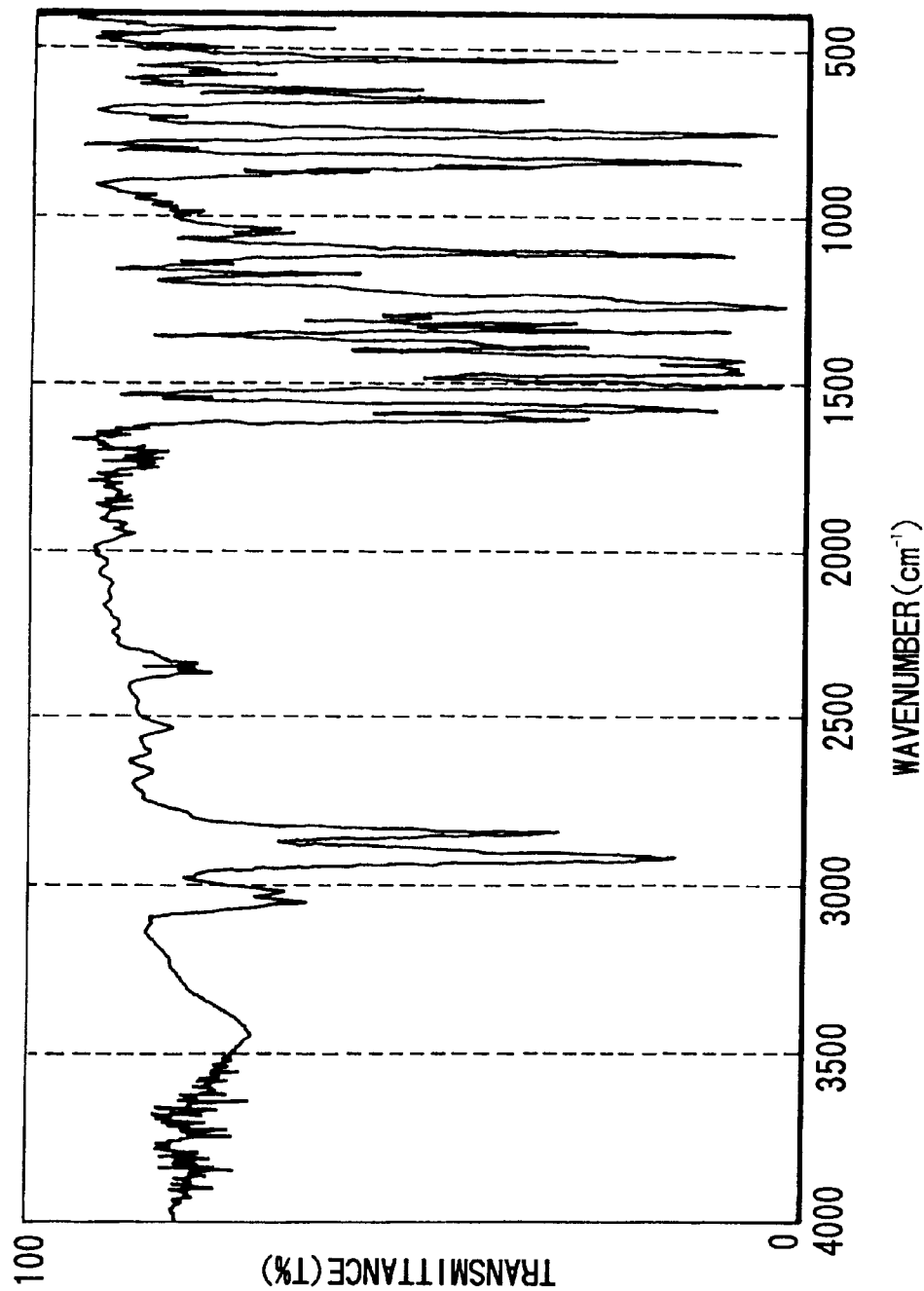

ORGANOELECTROLUMINESCENCE DEVICE MATERIAL AND ORGANOELECTROLUMINESCENCE DEVICE FOR WHICH THE MATERIAL IS ADAPTED

FIELD OF THE INVENTION

The present invention relates to an organoelectroluminescence ("EL" hereinafter) device used as a flat light source or display, more specifically to a light-emitting device having a high brightness.

PRIOR ART OF THE INVENTION

An EL device using an organic substance is greatly expected to be usable as a solid light-emitting inexpensive large-screen, full-color display device, and the development thereof is being made in many ways. Generally, an EL device is composed of a light-emitting layer and a pair of mutually opposite electrodes sandwiching the light-emitting layer. Light emission is the following phenomenon. When an electric field is applied between these two electrodes, the cathode injects electrons into the light-emitting layer, and the anode injects holes into the light-emitting layer. When the electrons recombine with the holes in the light-emitting layer, their energy level shifts to a valence bond band to release energy as fluorescent light.

As compared with inorganic EL devices, conventional organic EL devices require high voltage, and their light emission brightness and light emission efficiency are low. Further, conventional organic EL devices deteriorate in properties to a great extent, and no organic EL device has been put to practical use.

There has been recently proposed an organic EL device which is produced by laminating a thin film containing an organic compound having a fluorescent quantum effect of emitting light at a low voltage as low as less than 10 V, and it attracts attention (Appi. Phy. Lett., Vol. 51, page 913, 1987). The above organic EL device has a fluorescent layer containing a metal chelate complex and a hole-injecting layer containing an amine-based compound, and emits green light having a high brightness. The above organic EL device achieves nearly practically usable performance, since it accomplishes a brightness of 1,000 cd/m² and a maximum light emission efficiency of 1.5 lm/W at a direct current voltage of 6 or 7V.

However, conventional organic EL devices including the above organic EL device are not yet satisfactory in brightness although these organic EL devices are improved in brightness to some extent. The serious problem is that they are insufficient in lightemission stability in their continuous operation for a long period of time. Fewer materials which emit blue light perform adequate brightness or light emission efficieny,and it has been desired to develop light-emitting materials for the device.

SUMMARY OF THE INVENTION

It is an object of the present invention to provide a material which can give an organic EL device an excellent stability in the repetitive operation, and an organic EL device for which the material is adapted.

It is another object of the present invention to provide a material which can give an organic EL device which has a high light emission brightness and has excellent stability in the repetitive operation, and an organic EL device for which the material is adapted.

According to the present invention, there is provided an organic EL device material (gallium complex) of the general formula (1),

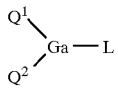

(1)

wherein each of $Q^1$ and $Q^2$ is independently a ligand of the general formula (2),l and L is a halogen atom, a substituted or unsubstituted alkyl group, a substituted or unsubstituted cycloalkyl group, a substituted or unsubstituted aryl group, a substituted or unsubstituted heterocyclic ring group, —$OR^1$ in which $R^1$ is a hydrogen atom, a substituted or unsubstituted alkyl group, la substituted or unsubstituted cycloalkyl group, a substituted or unsubstituted aryl group or a substituted or unsubstituted heterocyclic ring group, or —O—Ga—$Q^3(Q^4)$ in which $Q^3$ and $Q^4$ have the same meanings as those of $Q^1$ and $Q^2$,

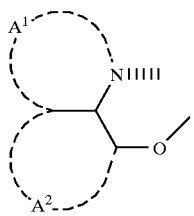

(2)

wherein $A^1$ and $A^2$ are substituted or unsubstituted six-membered aryl rings which are mutually fused to form a fused ring moiety.

According to the present invention, there is also provided an organic EL device comprising a light-emitting layer or a plurality of thin organic compound layers including the light-emitting layer, the light-emitting layer or a plurality of the thin organic compound layers being sandwiched between an anode and a cathode, wherein the light-emitting layer or at least one of a plurality of the thin organic compound layers contains the above organic EL device material (gallium complex).

BRIEF DESCRIPTION OF DRAWINGS

FIG. 6 is shows an infrared absorption spectrum of Compound (17).

DETAILED DESCRIPTION OF THE INVENTION

Figure 1:
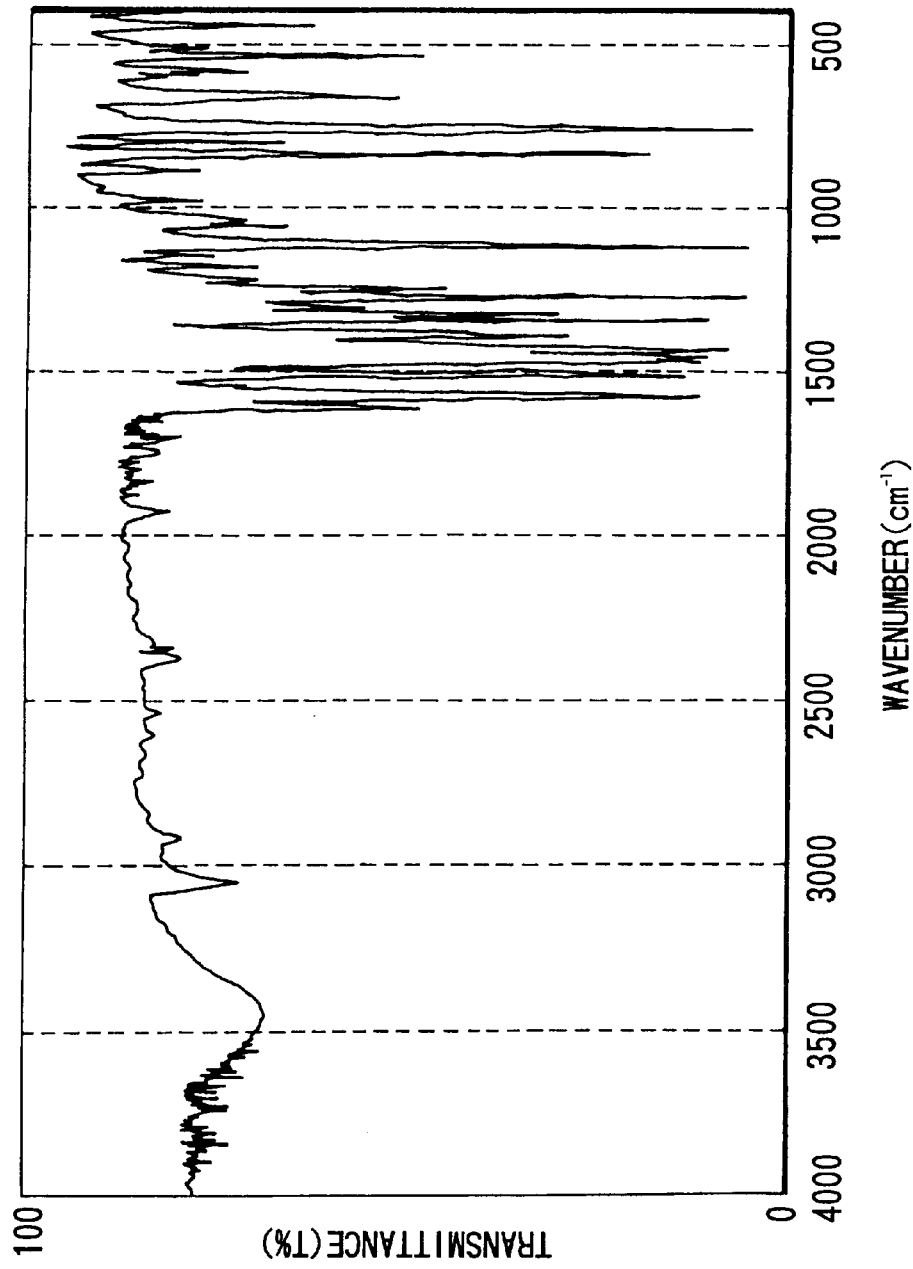
FIG. 1 is shows an infrared absorption spectrum of Compound (1).

In the general formula (1), the ligand represented by each of $Q^1$ to $Q^4$ includes quinoline moieties such as 8-hydroxyquinoline and 2-methyl-8-hydroxyquinoline, while the ligand shall not be limited to these.

In the general formula (2), $A^1$ and $A^2$ are substituted or unsubstituted six-membered aryl rings which are mutually fused to form a fused ring moiety. The fused ring moiety has the structure of an aryl ring or a heterocyclic ring. The metal complex in the present invention has a stronger quality as an n-type semiconductor and the high capability of injecting electrons. Further, since the formation energy at a complex formation time is low, the bonding strength of the metal and the ligands in the metal complex is high, and the fluorescence quantum efficiency as a light-emitting material is high.

Specific examples of the substituent on the fused ring of $A^1$ and $A^2$ forming the ligand of the general formula (2) include halogen atoms such las chlorine, bromine, iodine and fluorine; substituted or unsubstituted alkyl groups such as methyl, ethyl, propyl, butyl, sec-butyl, tert-butyl pentyl, hexyl, heptyl, octyl, stearyl and trichloromethyl; substituted or unsubstituted aryl groups such as phenyl, naphthyl, 3-methylphenyl, 3-methoxyphenyl, 3-fluorophenyl, 3-trichloromethylphenyl, 3-trifluoromethylphenyl and 3-nitrophenyl; substituted or unsubstituted alkoxy groups such as methoxy, n-butoxy, tert-butoxy, trichloromethoxy, trifluoroethoxy, pentafluoropropoxy, 2,2,3,3-tetrafluoropropoxy, 1,1,1,13,3,3-hexafluoro-2-propoxy and 6-(perfluoroethyl)hexyloxy; substituted or unsubstituted 15 aryloxy groups such as phenoxy, p-nitrophenoxy, p-tert-butylphenoxy, 3-fluorophenoxy, pentafluorophenoxy and 3-trifluoromethylphenoxy; substituted or unsubstituted alkylthio groups such as methylthio, tert-butylthio, hexylthio, octylthio and trifluoromethylthio; substituted or unsubstituted arylthio groups such as phenylthio, p-nitrophenylthio, p-tert-b tylphenylthio, 3-fluorophenylthio, pentafluorophenylthio and 3-trifluoromethylphenylthio; mono- or di-substituted amino groups such as methylamino, dimethylamino, ethylamino, diethylamino, dipropylamino, dibutylamino and diphenylamino; acylamino groups such as bis(acetoxymethyl)amino, bis(acetoxyethyl)amino, bis(acetoxypropyl)amino and bis(acetoxybutyl)amino; carbamoyl groups such as methylcarbamoyl, dimethylcarbamoyl, ethylcarbamoyl, diethylcarbamoyl, propylcarbamoyl, butylcarbamoyl and phenyicarbamoyl; carboxyl acid group; sulfonic acid group; imido group; cyano group; nitro group; amino group; hudroxyl group; siloxy group; acyl group; cycloalkyl groups such as cyclopentyl and cyclohexyl; aryl groups such as phenyl, naphthyl, biphenyl, anthranyl, phenahtryl, fluorenyl and pyrenyl; and heterocyclic groups such as pyrizinyl, pyrazinyl, pyrimidinyl, pyridazinyl, triazinyl, indolinyl, quinolinyl, acridinyl, pyrolidinyl, dioxanyl, piperidinyl, morpholinyl, piperazinyl, triathinyl, carbazolyl, furanyl, thiophenyl, oxazolyl, oxadiazolyl, penzoxazolyl, thiazolyl, thiadiazolyl, benzothiazoly, triazolyl, imidazolyl, benzoimidazolyl and puranyl. Further, any two members of the above substituents may bond together to form a six-membered ary ring or heterocyclic ring.

The gallium complex of the present invention can give an organic EL device having high performances. When the gallium complex of the present invention is used as a light-emitting material, there are obtained organic EL devices which exhibit high light emission efficiency in a broad light emission range of from blue to green. When the gallium complex of the present invention is used as a layer such as an electron-injecting layer or an electron-injection type light-emitting layer, which is in contact directly to a cathode, the device has the high capability of transporting electrons and the high capability of accepting electrons from a cathode, and the gallium complex of the present invention is therefore a remarkably advantageous material for an organic EL device. Further, most of the gallium complexes of the present invention have a melting point of at least 300° C., and this point is advantageous for manufacturing an organic EL device having a high light emission brightness and a long life.

The ligang L forming the gallium complex of the general formula (1) is a halogen atom, a substituted or unsubstituted alkyl group, a substituted or unsubstituted cycloalkyl group, a substituted or unsubstituted aryl group, a substituted or unsubstituted heterocyclic ring group, —OR$^1$ in which R$^1$ is a hydrogen atom, a substituted or unsubstituted alkyl group, a substituted or unsubstituted cycloalkyl group, a substituted or unsubstituted aryl group or a substituted or unsubstituted heterocyclic ring group, or —O—Ga—Q$^3$ (Q4) in which Q$^3$ and Q$^4$ have the same meanings as those of Q$^1$ and Q$^2$.

Specific examples of the ligand L or the substituents include those described concerning the rings $A^1$ and $A^2$.

The ligand L is preferably —OR$^1$. R$^1$ is a hydrogen atom, a substituted or unsubstituted alkyl group, a substituted or unsubstituted cycloalkyl group, a substituted or unsubstituted aryl group or a substituted or unsubstituted heterocyclic ring group. Q$^1$ or Q$^2$ in the general formula (1) is preferably a compound of the following general formula (3),

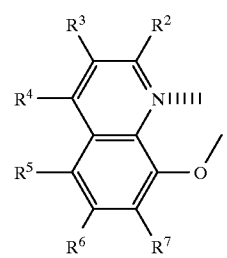

(3)

wherein each of R$^2$ to R$^7$ is independently a hydrogen atom, a halogen atom, cyano, nitro, a substituted or unsubstituted alkyl group, a substituted or unsubstituted cycloalkyl group, a substituted or unsubstituted aryl group or a substituted or unsubstituted heterocyclic ring group. Specific examples of the substituents include those described concerning the rings $A^1$ and $A^2$. Q$^1$ or Q$^2$ is particularly preferably a compound of the following formula (4).

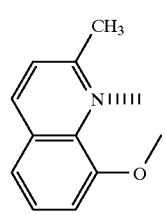

(4)

The gallium complex of the general formula (1), provided by the present invention, is synthesized, for example, from gallium as a metal or a gallium compound and compound(s) having ligand residues of Q$^1$ and Q$^2$ or L. The gallium compound includes alkyl gallium, gallium halide, gallium acetate, gallium nitrate, gallium arsenide, gallium nitride, gallium phosphide, gallium sulfide, gallium selenide, gallium telluride, galliumhydroxide, galliumoxide, galliumalkoxides such as trimethoxygallium, triethoxygallium and triisopropxyallium, and diethylgallium chloride. Part of each of these gallium compounds may be replaced with acetylacetonate. In view of reactivity and safety in the synthesis, gallium alkoxides are preferred although the gallium compound shall not be limited thereto. The ligand residue represented by $Q^1$ or $Q^2$ includes quinoline residues such as 8-hydroxyquinoline and 2-methyl-8-hydroxyquinoline.

The solvent used in the synthesis is selected from methanol, ethanol, isopropanol, ethyl acetate, acetonitrile, 1,4-dioxane, tetrahydrofuran, benzene, toluene, xylene, n-hexane, dimethylformamide, quinoline, sulfolaneorwater. The reaction temperature is determined depending upon the rate of the ligand forming the gallium complex. The temperature for the synthesis is preferably between 0° C. and 250° C., more preferably 20° C. and 80° C. The synthesis is carried out for 10 minutes to 24 hours. However, the synthesis conditions shall not be limited to the above-specified, since the synthesis conditions are determined depending upon the gallium compound, the ligand, the solvent and a catalyst used for the synthesis.

The gallium complex of the general formula (1) is obtained by reacting gallium or the above gallium compound with a ligand residue (ligand compound) having a great steric hindrance as a compound for forming ligand residues represented by $Q^1$ and $Q^2$, to bond two ligand residues per gallium atom. The ligand L optionally bonds to a residue and constitutes the gallium complex of the present invention. Gallium strongly bonds to an alkyl group, an oxygen atom and a halogen atom and can form a stable gallium complex. Further, it is difficult to form a stable aluminum complex with 8-hydroxyquinoline having an alkyl group on the 2-position such as 2-methyl-8-hydroxyquinoline, while gallium can form a stable gallium complex with such a 8-hydroxyquinoline having an alkyl group on the 2-position. Gallium is therefore advantageous in this point.

Table 1 specifically shows typical examples (Compounds (1) to (28)) of the compound of the general formula (1), although the compound of the general formula (1) shall not be limited to these.

TABLE 1

| Compound | Chemical structure |
|---|---|
| (1) | (2-methyl-8-hydroxyquinoline)$_2$Ga—Cl |
| (2) | (2-methyl-8-hydroxyquinoline)$_2$Ga—Br |
| (3) | (8-hydroxyquinoline)$_2$Ga—CH$_3$ |
| (4) | (8-hydroxyquinoline)$_2$Ga—OC$_2$H$_5$ |

TABLE 1-continued
| Compound | Chemical structure |
|---|---|
| (5)–(10) | 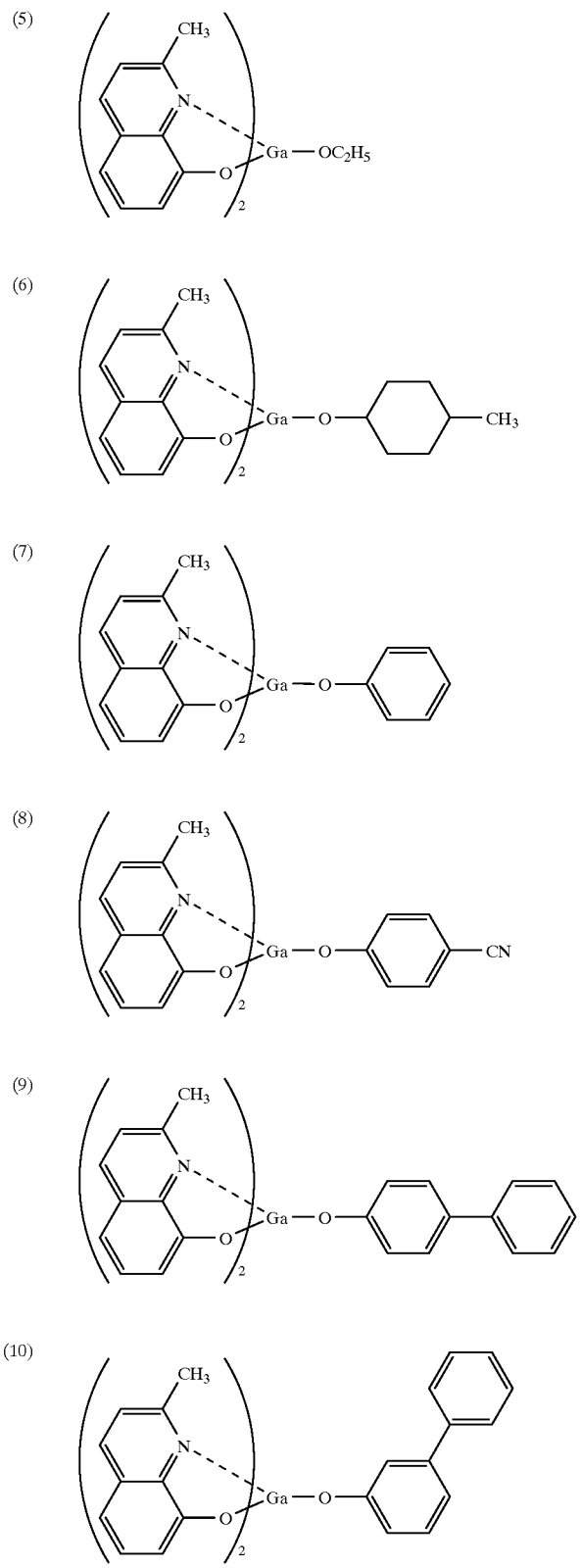 |

TABLE 1-continued

| Compound | Chemical structure |
|---|---|
| (11) | *(structure: bis(2-methyl-8-quinolinolato)gallium with O-biphenyl ligand)* |
| (12) | *(structure: bis(2-methyl-8-quinolinolato)gallium with O-(4-cyclohexylphenyl) ligand)* |
| (13) | *(structure: bis(2-methyl-8-quinolinolato)gallium with O-(4'-cyano-4-biphenyl) ligand)* |
| (14) | *(structure: bis(2-methyl-8-quinolinolato)gallium with O-(4-cumyl-phenyl) ligand)* |
| (15) | *(structure: bis(2-methyl-8-quinolinolato)gallium with O-(4-phenoxyphenyl) ligand)* |
| (16) | *(structure: bis(2-methyl-8-quinolinolato)gallium with O-(1-naphthyl) ligand)* |
| (17) | *(structure: bis(2-methyl-8-quinolinolato)gallium with O-(2-naphthyl) ligand)* |

TABLE 1-continued
| Compound | Chemical structure |
|---|---|
| (18) | 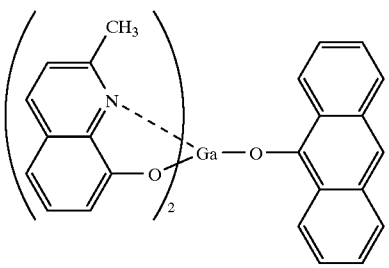 |
| (19) | 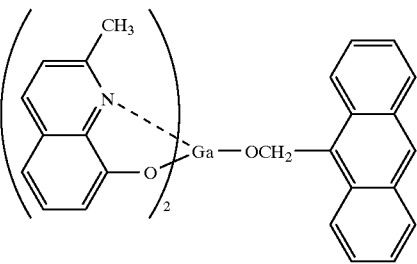 |
| (20) | 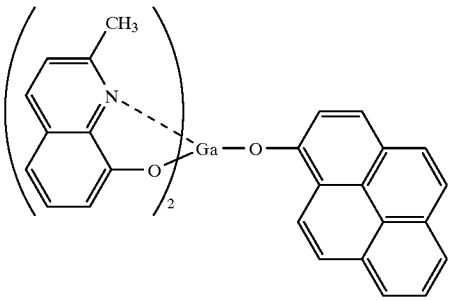 |
| (21) | 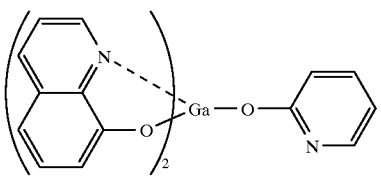 |
| (22) | 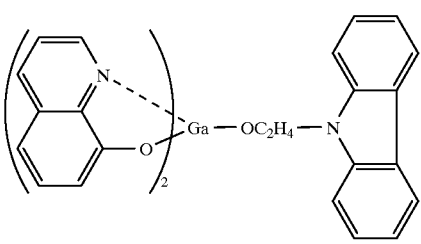 |
| (23) | 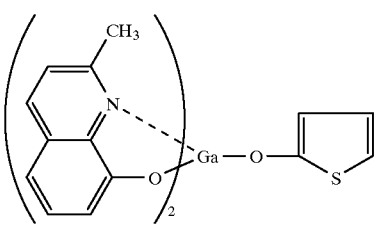 |

TABLE 1-continued

| Compound | Chemical structure |
|---|---|
| (24) | [gallium complex with 2-methylquinolin-8-olato ligands and OCH$_2$-thiophene] |
| (25) | [bis(8-quinolinolato)gallium–O–gallium(8-quinolinolato)$_2$ μ-oxo dimer] |
| (26) | [μ-oxo bis[bis(2-methyl-8-quinolinolato)gallium] complex] |
| (27) | [μ-oxo bis[bis(benzo[g]quinolin-10-olato)gallium] complex] |
| (28) | [μ-oxo bis[bis(5-phenyl-8-quinolinolato)gallium] complex] |

The above gallium complex can be adjusted to one having a necessary purity by cleaning it with water and/or an organic solvent, recrystallization from a proper solvent, a sublimation purification method or a combination of these.

The organic EL device is a device manufactured by forming one or more organic thin layers between an anode and a cathode. In a mono-layer organic EL device, a light-emitting layer is formed between an anode and a cathode. The light-emitting layer contains a light-emitting material, and the light-emitting layer may further contain a hole-injecting material for transporting holes injected from the anode to the light-emitting material or an electron-injecting material for transporting electrons injected from the cathode to the light-emitting material. The organic EL device of a multi-layer type has a layer structure such as anode/hole-injecting layer/light-emitting layer/cathode, anode/light-emitting layer/electron-injecting layer/cathode, or anode/hole-injecting layer/light-emitting layer/electron-injecting layer/cathode. The compound of the general formula (1) can transport holes or electrons, while it can be used in the electron-injecting layer since it is superior in the capability of transporting electrons. Further, the compound of the general formula (1) can be used as a light-emitting layer since EL devices having light-emitting layers containing compounds of the general formula (1) emit fluorescence of intense blue to intense green. Therefore, the compound of the general formula (1) can give an organic EL device having high light emission characteristics.

A multi-layer structure of the organic EL device can serve to prevent quenching from degrading the brightness and the device life. Further, at least two members of a light-emitting material, a dopant, and a hole-injecting material and an electron-injecting material for carrier transportation may be used in combination. Further, each of the hole-injecting layer, the light-emitting layer and the electron-injecting layer may have the structure of at least two layers, and a device structure is selected such that holes or electrons can be effectively injected from the anode or the cathode and effectively transported through a layer.

When the gallium complex of the present invention is used as an electron-injecting material, the light-emitting material or the dopant which can be used together is selected from known materials such as naphthalene, anthracene, phenanthrene, pyrene, tetracene, coronene, chrysene, fluorescein, perylene, phthaloperylene, naphthaloperylene, perinone, naphthaloperinone, diphenylbutadiene, tetraphenylbutadiene, coumarine, oxadiazole, aldazine, bisbenzoxazoline, bisstyryl, diamine, pyrazine, cyclopentadiene, quinoline metal complex, aminoquinoline metal complex, benzoquinoline metal complex, imine, diphenylethylene, vinyl anthracene, diaminocarbazole, pyrane, thiopyrane, polymethine, merocyanine, an imidazole-chelated oxynoid compound, quinacridone, rubrene and derivatives of these, although the above materials shall not be limited to these. In particular, a metal complex compound, a bisstyryl compound, a conjugated polymer and an arylamine derivative are suitable as a light-emitting material.

The above metal complex compound includes lithium (8-hydroxyquinolinate), zinc bis(8-hydroxyquinolinate), manganese bis(8-hydroxyquinolinate), copper bis(8-hydroxyquinolinate), aluminum tris(8-hydroxyquinolinate), gallium tris(8-hydroxyquinolinate), beryllium bis(10-hydroxybenzo[h]quinolinate), zinc bis(10-hydroxybenzo[h]quinolinate), magnesium bis(10-hydroxybenzo[h]quinolinate), aluminum tris(10-hydroxybenzo[h]quinolinate, chlorogallium bis(2-methyl-8-quinolinate), gallium bis(2-methyl-8-quinolinate)(o-cresolate), aluminum bis(2-methyl-8-quinolinate)(1-phenolate), gallium bis(2-methyl-8-quinolinate)(2-phenolate), aluminum bis(2-methyl-8-quinolinate)(1-naphtholate), gallium bis(2-methyl-8-quinolinate)(1-naphtholate), zinc bis(2-[2-benzoxazolinate]phenolate), and zinc bis(2-[2-benzothiazolinate]phenolate. The above compounds may be used alone or in combination.

The above bisstyryl compound includes divalent residues which may have a substrate as a binding group such as phenylene residue, naphthylene residue, biphenylene residue, anthranylene residue, pyrenylene residue, thiophenylene residue, triphenylamine residue and N-ethylcarbazole residue. Specific examples of the bisstyryl compound include diphenylamino-1,4-bisstyrylbenzene, ditrylamino-1,4-bisstyrylbenzene, diphenylamino-4,4'-bisstyrylbiphenyl, 3-(N-ethylcarbazole)-4,4'-bisstyrylbiphenyl, and bis(4,4'-[2,2-diphenylvinyl]) biphenyl. The above compounds may be used alone or in combination.

The conjugated polymer is a polymer having 2 to 10,000 recurring units, obtained by polymerizing only an arylene which may contain a nitrogen, oxygen or sulfur atom, or by polymerizing the arylene and a conjugated compound such as a vinyl compound. Specific examples of the cojugated polymer include poly(p-phenylene), poly(o-thiphene), poly(p-phenylenevinylene), poly(2,5-dipentyl-p-phenylenevinylene), poly(2,5-dipentyl-m-phenylenevinylene), poly(2,5-dioctyl-p-phenylenevinylene), poly(2,5-dihexyloxy-p-phenylenevinylene), poly(2,5-dihexyloxy-m-phenylenevinylene), poly(2,5-dihexylthio-p-phenylenevinylene), poly(2,5-didecyloxy-p-phenylenevinylene), poly(2-methoxy-5-hexyloxy-p-phenylenevinylene), poly(2,5-thienylenevinylene), poly(3-n-octyl-2,5-thienylenevinylene), poly(1,4-naphthalenevinylene), poly(9,10-anthracenevinylene) and a copolymer obtained from at least two members of these. The above compounds may be used alone or in combination.

The above arylamine derivative is a compound obtained by substituting a substituted diamino group in an arylene which may contain a nitrogen, oxygen or sulfur atom. Specific examples of the arylamine derivative include N,N,N',N'-(4-methylphenyl)-1,4'-phenyl-4,4'-diamine, N,N,N',N'-(4-methylphenyl)-1,3'-phenyl-4,4'-diamine, N,N'-diphenyl-N,N'-(3-methylphenyl)-1,1'-biphenyl-4,4'-diamine, N,N'-(4-methylphenyl)-N,N'-(4-n-butylphenyl)-phenathrene-9,10-dimaine, N,N'-diphenyl-N,N'-dinaphthyl-1,1'-biphenyl-4,4'-diamine, N,N,N',N'-(4-methylphenyl)-1,4-naphthyl-4,4'-diamine, N,N,N',N'-(4-n-octylphenyl)-9,10-anthranyl-4,4'-dimaine, and N,N,N',N'-[4-(α,α'-dimethylbenzyl)phenyl]-anthranyl-9,10-diamine. The above compounds may be used alone or in combination.

The hole-injecting material is a material which is capable of transporting holes, receiving holes from an anode, injecting holes into a light-emitting layer or light-emitting material, preventing excitons generated in a light-emitting layer from moving an electron-injecting layer or electron-injecting material and forming a thin film. Although not specially limited, specific examples of the hole-injecting material include a phthalocyanine derivative, a naphthalocyanine derivative, a porphyrin derivative, oxadiazole, triazole, imidazole, imidazolone, imidazolthione, pyrazoline, pyrazolone, tetrahydroimidazole, hydrazone, acylhydrazone, polyarylalkane, stilbene, butadiene, benzidine type triphenylamine, styrylamine type triphenylamine, diamine type triphenylamine, derivatives of these, and polymer materials such as polyvinylcarbazole, polysilane and an electrically conductive polymer.

When the gallium complex of the present invention is used as a light-emitting material, the electron-injecting material that can be used together is a material which is capable of transporting electrons, receiving electrons from a cathode, injecting electrons into a light-emitting layer or light-emitting material, preventing excitons generated in the light-emitting layer from moving into a hole-injecting layer or hole-injecting material and forming a thin film. Although not specially limited, examples of the electron-injecting material include fluorenone, anthraquinodimethane, diphenoquinone, thiopyran dioxide, oxadiazole, thiadiazole, triazole, tetrazole, imidazole, perylenetetracarboxylic acid, fluorenylidenemethane, anthraquinodimethane, anthrone, a metal complex and derivatives of these. The hole-injecting material may be sensitivity-increased by incorporating an electron-accepting material, and the electron-injecting material may be sensitivity-increased by incorporating an electron-donating material. Further, the hole-injecting material can be selected from the above hole-injecting materials.

The gallium complex of the present invention can be used as a light-emitting material in a light-emitting layer. The light-emitting layer may contain at least one selected from a light-emitting material, a dopant, a hole-injecting material or an electron-injecting material in combination with the gallium complex of the present invention. Further, the gallium complex of the present invention can be used in/as an electron-injecting layer between a light-emitting layer and a cathode since it is highly capable of receiving electrons from a cathode of a metal and transporting the electrons.

The electrically conductive material used for the anode of the organic EL device is suitably selected from those materials having a work function of greater than 4 eV. This electrically conductive material includes carbon, aluminum, vanadium, iron, cobalt, nickel, tungsten, silver, gold, platinum, palladium, alloys of these, metal oxides such as tin oxide and indium oxide used for ITO substrates or NESA substrates, and organic electrically conductive resins such as polythiophene and polypyrrole.

The electrically conductive material used for the cathode is suitably selected from those having a work function of smaller than 4 eV. This electrically conductive material includes magnesium, calcium, tin, lead, titanium, yttrium, lithium, ruthenium, manganese, aluminum and alloys of these, while it shall not be limited to these. Typical examples of the alloys include magnesium/silver, magnesium/indium and lithium/aluminum, while the alloys shall not be limited to these. The metal ratio of the alloy is properly controlled by controlling the temperature of a deposition source, atmosphere and the degree of vacuum. Each of the anode and the cathode may have a structure of at least two layers as required.

For the effective light emission of the organic EL device, at least one of the electrodes is desirably transparent inthelightemissionwavelengthregionofthedevice. Further, the substrate is desirably transparent. The transparent electrode is produced from the above electrically conductive material by a deposition method or a sputtering method such that a predetermined transparency is secured. The electrode which forms a light emission surface preferably has a light transmittance of at least 10%. The substrate is not specially limited if it has adequate mechanical and thermal strength and is transparent. For example, it is selected from glass substrates and substrates of transparent resins such as a polyethylene substrate, a polyethylene terephthalate substrate, a polyether sulfone substrate and a polypropylene substrate.

Each of the layers forming the organic EL device of the present invention can be formed by any one of dry film forming methods such as a vacuum deposition method, a sputtering method, a plasma method and an ion plating method and wet film forming methods such as a spin coating method, a dipping method and a flow coating method. The thickness of each layer is not specially limited, while each layer is required to have a proper thickness. When the layer thickness is too large, inefficiently, a high voltage is required to achieve predetermined emission of light. When the layer thickness is too small, the layer is liable to have a pinhole, etc., so that sufficient light emission brightness is hard to obtain when an electric field is applied. Generally, the thickness of each layer is preferably in the range of from 5 nm to 10 μm, more preferably 10 nm to 0.2 μm.

In the wet film forming method, a material for forming an intended layer is dissolved or dispersed in a proper solvent, and a thin film is formed from the solution or dispersion. The solvent is selected from ethanol, chloroform, tetrahydrofuran and dioxane, while the solvent shall not be limited to these. For improving the film formability and preventing the occurrence of pinholes, the above solution or dispersion for forming the layer may contain a proper resin and a proper additive. The resin suitable for use in the present invention includes insulating resins such as polystyrene, polycarbonate, polyarylate, polyester, polyamide, polyurethane, polysulfone, polymethyl methacrylate, polymethyl acrylate and cellulose, copolymers of these, photoconductive resins such as poly-N-vinylcarbozole and polysilane, and electrically conductive resins such as polythiophene and polypyrrole. The above additive includes an antioxidant, an ultraviolet absorbent and a plasticizer.

For improving the organic EL device of the present invention in the stability against temperature, humidity and ambient atmosphere, a protective layer may be formed on the surface of the device, or the device as a whole may be sealed with a silicone oil, or the like.

In the present invention, the organic EL device has a light-emitting layer or an electron-injecting layer which contains the gallium complex of the general formula (1), and the organic EL device is therefore improved in properties such as light emission efficiency, maximum light emission brightness, etc. Further, the organic EL device is highly stable against heat and electric current, and further it exhibits practically usable light emission brightness at a low voltage, so that the deterioration of the device, a vital problem of prior art devices, can be remarkably decreased.

The organic EL device of the present invention can be applied to a flat panel display of a wall-mountable TV set, a light source for a copying machine or a printer, a light source for a liquid crystal display or a counter, a display board and a sign lamp as aa flat light-emitter. The organic EL device of the present invention is therefore greatly industrially valuable.

EXAMPLES

The present invention will be further explained with reference to Examples hereinafter. Examples used glass substrates with ITO electrode having a surface resistance of 10 ($\Omega/\square$) for producing organic EL devices.

Synthesis Example 1

5.0 Grams of anhydrous gallium trichloride and 100 ml of anhydrous ethanol were placed in a flask and stirred. Further, a solution of 9.0 g of 8-hydroxyquinaldine in 100 ml of anhydrous ethanol was dropwise added. The mixture was stirred at room temperature for 1 hour to precipitate a solid, and the solid was recovered by filtration, washed with anhydrous ethanol and vacuum-dried to give 8.9 g of a yellowish white powder. The yellowish white powder was subjected to elemental analysis and mass analysis and measured for infrared absorption spectrum and NMR spectrum to show that the powder was Compound (1). FIG. 1 shows the infrared absorption spectrum of Compound (1).

Synthesis Example 2

Figure 2:
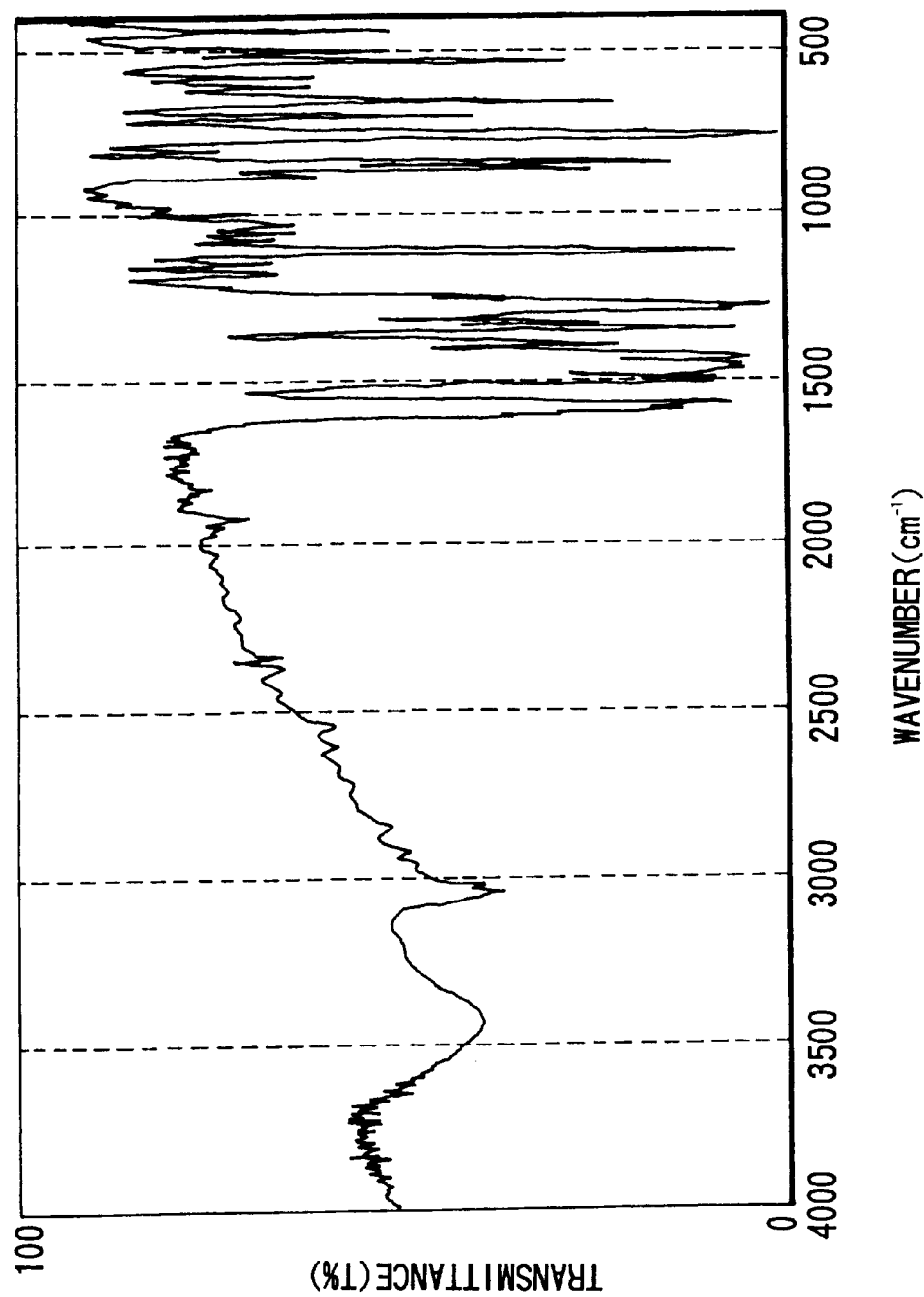
FIG. 2 is shows an infrared absorption spectrum of Compound (2).

5.0 Grams of trimethoxygallium and 100 g of anhydrous ethanolwereplacedinaflaskandstirred. Further,asolution of 9.0 g of 8-hydroxyquinaldine in 140 g of anhydrous ethanol was dropwise added, and the mixture was stirred at 60° C. for 30 minutes. Further, 2.9 g of phenol was added, and the mixture was stirred at 70° C. for 30 minutes. Then, 4.9 g of 8-hydroxyquinaldine was added, and the mixture was stirred at 70° C. for5hourstoprecipitateasolid. The solid was recovered by filtration, washed with anhydrous ethanol and vacuum-dried to give 6.3 g of a yellowish white powder. The yellowish white powder was subjected to elemental analysis and mass analysis and measured for infrared absorption spectrum and NMR spectrum to show that the powder was Compound (7). FIG. 2 shows the infrared absorption spectrum of Compound (7).

Synthesis Example 3

Figure 3:
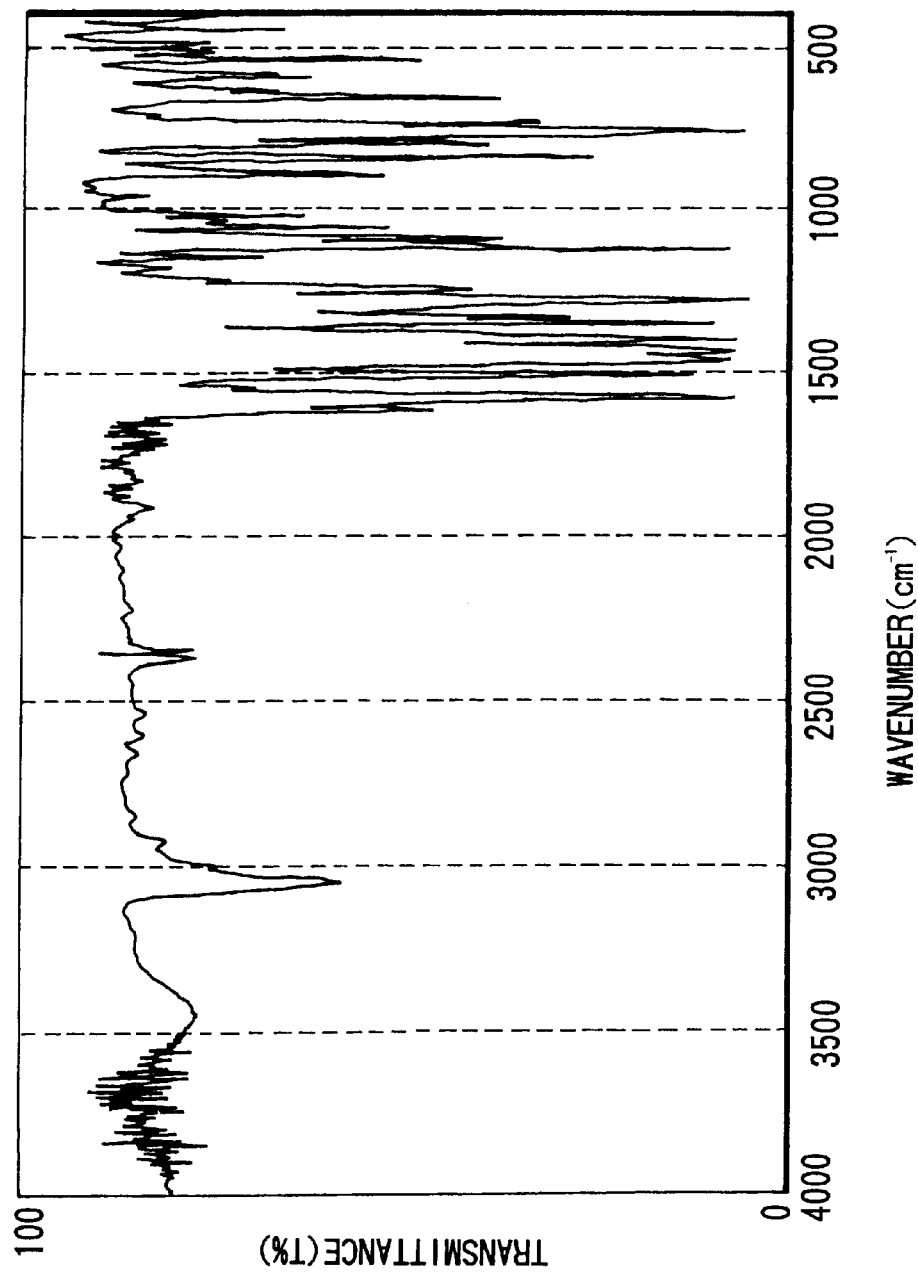
FIG. 3 is shows an infrared absorption spectrum of Compound (9).

5.0 Grams of trimethoxygallium and 100 g of anhydrous ethanol were placed in a flask and stirred. Further, a solution of 9.0 g of 8-hydroxyquinaldine in 140 g of anhydrous ethanol was dropwise added, and the mixture was stirred at 60° C. for 30 minutes. Further, 5.3 g of 4-hydroxybiphenyl was added, and the mixture was stirred at 70° C. for 30 minutes. Then, 4.9 g of 8-hydroxyquinaldine was added, and the mixture was stirred at 70° C. for 5 hours to precipitate a solid. The solid was recovered by filtration, washed with anhydrous ethanol and vacuum-dried to give 7.2 g of a yellowish white powder. The yellowish white powder was subjected to elemental analysis and mass analysis and measured for infrared absorption spectrum and NMR spectrum to show that the powder was Compound (9). FIG. 3 shows the infrared absorption spectrum of Compound (9).

Synthesis Example 4

Figure 4:
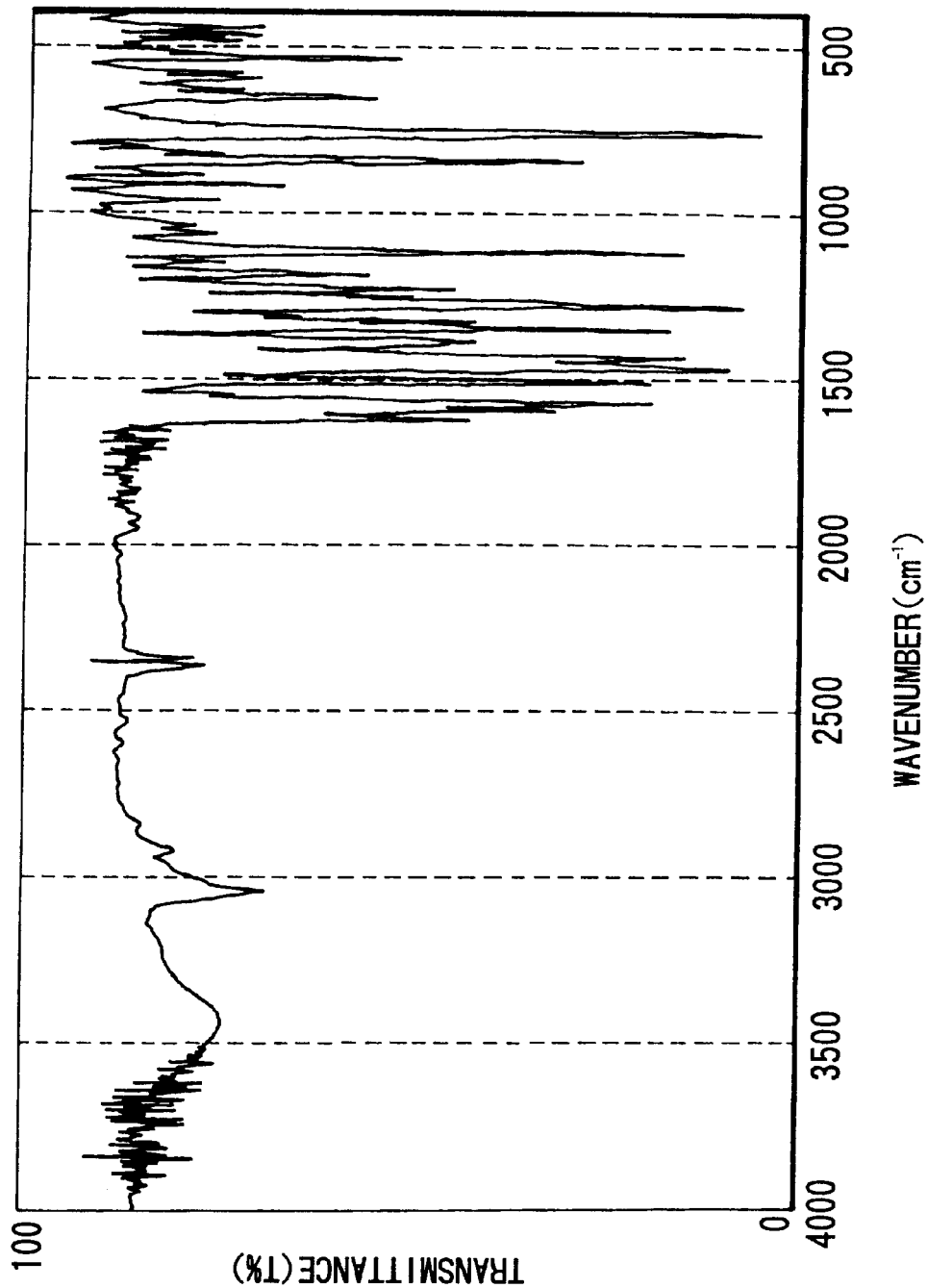
FIG. 4 is shows an infrared absorption spectrum of Compound (12).

7.2 Grams of triisopropoxygallium and 100 g of anhydrous ethanol were placed in a flask and stirred. Further, a solution of 9.0 g of 8-hydroxyquinaldine in 140 g of anhydrous ethanol was dropwise added, and the mixture was stirred at 60° C. for30 minutes. Further,5.5 g of 4-cyclohexylphenolwasadded, and the mixture was stirred at 70° C. for 30 minutes. Then, 4.9 g of 8-hydroxyquinaldine was added, and the mixture was stirred at 70° C. for 5 hours to precipitate a solid. The solid was recovered by filtration, washed with anhydrous ethanol and vacuum-dried to give 7.4 g of a yellowish white powder. The yellowish white powder was subjected to elemental analysis and mass analysis and measured for infrared absorption spectrum and NMR spectrum to show that the powder was Compound (12). FIG. 4 shows the infrared absorption spectrum of Compound (12).

Synthesis Example 5

Figure 5:
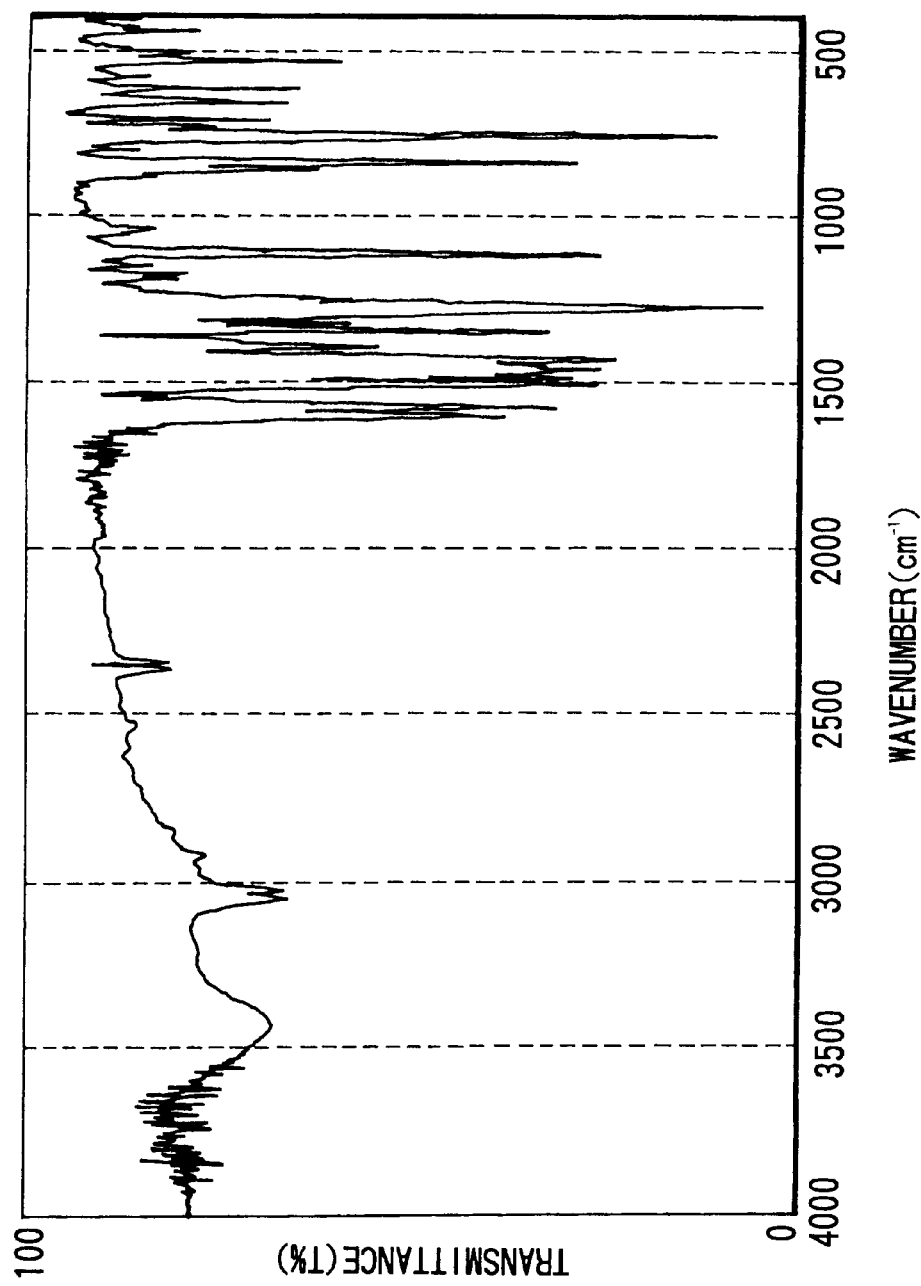
FIG. 5 is shows an infrared absorption spectrum of Compound (16).

5.0 Grams of trimethoxygallium and 100 g of anhydrous ethanol were placed in a flask and stirred. Further, a solution of 9.0 g of 8-hydroxyquinaldine in 140 g of anhydrous ethanol was dropwise added, and the mixture was stirred at 60° C. for 30 minutes. Further, 4.5 g of 1-naphthol was added, and the mixture was stirred at 70° C. for 30 minutes. Then, 4.9 g of 8-hydroxyquinaldine was added, and the mixture was stirred at 70° C. for 5 hours to precipitate a solid. The solid was recovered by filtration, washed with anhydrous ethanol and vacuum-dried to give 6.5 g of a yellowish white powder. The yellowish white powder was subjected to elemental analysis and mass analysis and measured for infrared absorption spectrum and NMR spectrum to show that the powder was Compound (16). FIG. 5 shows the infrared absorption spectrum of Compound (16).

Synthesis Example 6

5.0 Grams of trimethoxygallium and 100 g of anhydrous ethanol were placed in a flask and stirred. Further, a solution of 9.0 g of 8-hydroxyquinaldine in 140 g of anhydrous ethanol was dropwise added, and the mixture was stirred at 60° C. for 30 minutes. Further, 4.5 g of 2-naphthol was added, and the mixture was stirred at 70° C. for 30 minutes. Then, 4.9 g of 8-hydroxyquinaldine was added, and the mixture was stirred at 70° C. for 5 hours to precipitate a solid. The solid was recovered by filtration, washed with anhydrous ethanol and vacuum-dried to give 6.6 g of a yellowish white powder. The yellowish white powder was subjected to elemental analysis and mass analysis and measured for infrared absorption spectrum and NMR spectrum to show that the powder was Compound (17). FIG. 7 shows the infrared absorption spectrum of Compound (17).

Synthesis Example 7

9.0 Grams of 8-hydroxyquinaldine, 11.5 g of gallium-di-isopropoxy-acetaylacetate and 200 ml of toluene were placed in a flask and stirred at room temperature for 20 hours. The resultant solution was distilled at 50° C. under vacuum (under reduced pressure) to evaporate the toluene, whereby a compound in the form of a yellow paste was obtained. The so-obtained compound was washed with toluene and vacuum-dried to give 8.7 g of a yellowish white powder. The yellowish white powder was subjected to elemental analysis and mass analysis and measured for infrared absorption spectrum and NMR spectrum to show that the powder was Compound (26).

In the following Examples, the gallium complex of the present invention was used as a light-emitting material in a light-emitting layer.

Example 1

Compound (29) having the following chemical structure was vacuum-deposited on a cleaned glass plate with an ITO electrode to form a hole-injecting layer having a thickness of 50 mm. Then, Compound (1) as a light-emitting material was vacuum-deposited thereon to form a light-emitting layer having a thickness of 50 nm. An electrode having a thickness of 150 nm was formed thereon from a magnesium/silver alloy having a magnesium/silver mixing ratio of 10/1, to obtain an organic EL device. The hole-injecting layer, the light-emitting layer and the cathode were formed under a vacuum of $10^{-6}$ Torr at a substrate temperature of room temperature. The organic EL device showed a blue light emission of 6,800 (cd/m$^2$) at a direct current voltage of 12 V, a light emission efficiency of 0.52 (lm/W) and a chromaticity of x=0.290 and y=0.430.

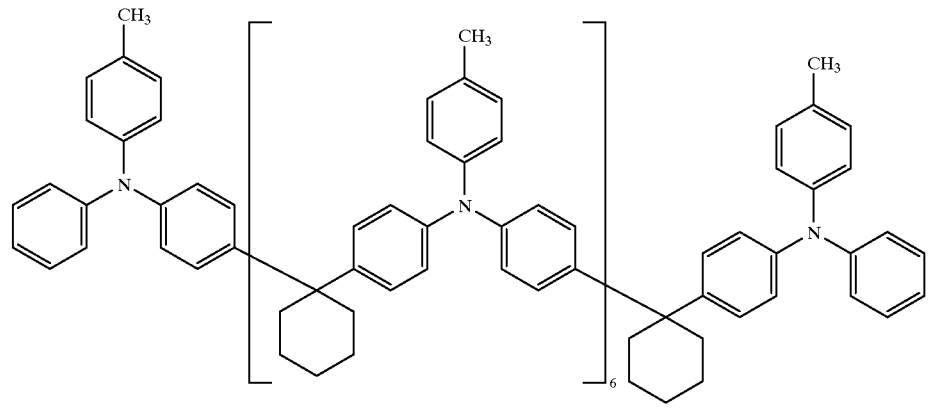

The above organic EL device was measured for a light emission brightness with an LS-100 (supplied by Minolta Camera Co., Ltd.). The light emission efficiency η (lm/W) was determined on the basis of the following equation, $$\eta(lm/W) = \pi \cdot L_0(cd/m^2)/P_{in}(W/m^2)$$

in which $P_{in}$ is an applied power per unit area and $L_0$ is a brightness obtained by the measurement. In this case, a complete diffusion surface is assumed.

Organic EL devices obtained in Examples hereinafter were also measured for brightness and determined for light emission efficiency in the above manner.

Examples 2–16

Organic EL devices were prepared in the same manner as in Example 1 except that the light-emitting material was replaced with compounds shown in Table 2. The organic EL devices were measured for light emission brightnesses at a direct current voltage of 12 V and light emission efficiencies. Table 2 shows the results.

TABLE 2

| Example | Compound | Brightness (cd/m²) | Light emission efficiency (lm/W) |
| --- | --- | --- | --- |
| 2 | (2) | 6,500 | 0.53 |
| 3 | (3) | 6,000 | 0.51 |
| 4 | (6) | 6,000 | 0.50 |
| 5 | (4) | 6,800 | 0.55 |
| 6 | (5) | 7,100 | 0.61 |
| 7 | (7) | 6,900 | 0.57 |
| 8 | (9) | 7,000 | 0.57 |
| 9 | (18) | 7,000 | 0.53 |
| 10 | (20) | 6,800 | 0.55 |
| 11 | (19) | 6,800 | 0.55 |
| 12 | (21) | 6,300 | 0.52 |
| 13 | (22) | 6,500 | 0.54 |
| 14 | (25) | 6,600 | 0.55 |
| 15 | (26) | 7,200 | 0.63 |
| 16 | (27) | 6,000 | 0.50 |

Example 17

Compound (1) and poly-N-vinylcarbazole in a Compound (1)/poly-N-vinylcarbazole weight ratio of ⅗ were dissolved and dispersed in chloroform, and the solution was spin-coated on a cleaned glass substrate with an ITO electrode to form a light-emitting layer having a thickness of 100 m. Then, an electrode having a thickness of 150 nm was formed thereon from a magnesium/silver alloy having a magnesium/silver mixing ratio of 10/1, to obtain an organic EL device. The cathode was formed by deposition under a vacuum of $10^{-6}$ Torr at a substrate temperature of room temperature. The organic EL device showed a blue light emission of 1,000 (cd/m²) at a direct current voltage of 12 V and a light emission efficiency of 0.23 (lm/W).

Example 18

Compound (18), 2-(4-tert-butylphenyl)-5-(biphenyl)-1,3, 4-oxadiazole, Compound (30) having the following chemical formula and a polycarbonate resin in a weight ratio of 3/2/3/2 were dissolved and dispersed in chloroform, and the solution was spin-coated on a glass substrate with an ITO electrode to form a light-emitting layer having a thickness of 100 nm. Then, an electrode having a thickness of 150 nm was formed thereon from a magnesium/silver alloy having a magnesium/silver mixing ratio of 10/1, to obtain an organic EL device. The cathode was formed by deposition under a vacuum of $10^{-6}$ Torr at a substrate temperature of room temperature. The organic EL device showed a bluish green light emission of 1,500 (cd/m²) at a direct current voltage of 12 V and a light emission efficiency of 0.42 (lm/W).

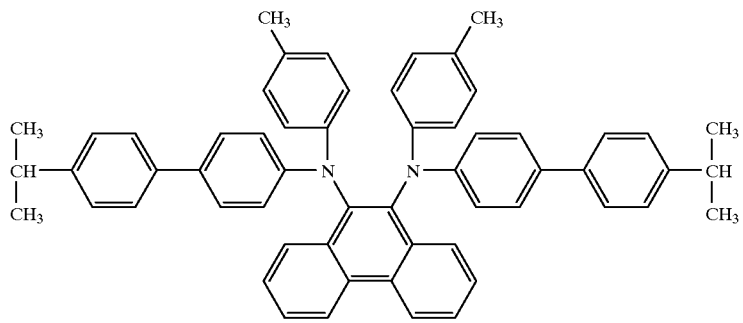

Example 19

Compound (29) was dissolved and dispersed in chloroform, and the solution was spin-coated on a cleaned glass substrate with an ITO electrode to form a hole-injecting layer having a thickness of 30 nm. Then, Compound (26) was vapor-deposited thereon to form a light-emitting layer having a thickness of 50 nm. Further, 2-(4-tert-butylphenyl)-5-(biphenyl)-1,3,4-oxadiazole was vacuum-deposited thereon to form an electron-injecting layer having a thickness of 20 nm. Then, an electrode having a thickness of 150 nm was formed thereon from a magnesium/silver alloy having a magnesium/silver mixing ratio of 10/1, to obtain an organic EL device. The light-emitting layer, the electron-injecting layer and the cathode were formed by deposition under a vacuum of $10^{-6}$ Torr at a substrate temperature of room temperature. The organic EL device showed a bluish green light emission of 6,500 (cd/m²) at a direct current voltage of 12 V and a light emission efficiency of 0.65 (lm/W).

Example 20

Compound (29) was vacuum-deposited on a cleaned glass substrate with an ITO electrode to form a hole-injecting layer having a thickness of 30 nm. Then, Compound 7 was vapor-deposited thereon to form a light-emitting layer having a thickness of 30 nm. Further, Compound (25) was vacuum-deposited thereon to form an electron-injecting layer having a thickness of 20 nm. Then, an electrode having a thickness of 150 nm was formed thereon from a magnesium/silver alloy having a magnesium/silver mixing ratio of 10/1, to obtain an organic EL device. The hole-injecting layer, the light-emitting layer, the electron-injecting layer and the cathode were formed by deposition under a vacuum of $10^{-6}$ Torr at a substrate temperature of room temperature. The organic EL device showed a blue light emission of 6,300 ($cd/m^2$) at a direct current voltage of 12 V and a light emission efficiency of 0.68 (lm/W).

Example 21

Compound (31) having the following chemical structure was vacuum-deposited on a cleaned glass substrate with an ITO electrode to form a hole-injecting layer having a thickness of 30 mm. Then, Compound (7) was vapor-deposited thereon to form a light-emitting layer having a thickness of 40 nm. Further, Compound (17) was vacuum-deposited thereon to form an electron-injecting layer having a thickness of 20 nm. Then, an electrode having a thickness of 150 nm was formed thereon from a magnesium/silver alloy having a magnesium/silver mixing ratio of 10/1, to obtain an organic EL device. The hole-injecting layer, the light-emitting layer, the electron-injecting layer and the cathode were formed by deposition under a vacuum of $10^{-6}$ Torr at a substrate temperature of room temperature. The organic EL device showed a blue light emission of 16,000 ($cd/m^2$) at a direct current voltage of 8 V and a light emission efficiency of 2.04 (lm/W).

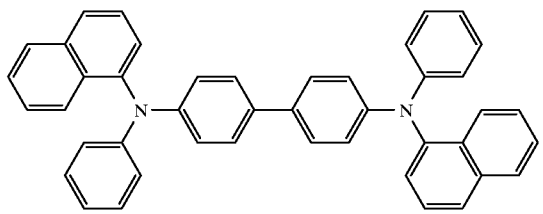

In the following Examples, the gallium complex of the present invention was used as an electron-injecting material in an electron-injecting layer.

Example 22

Compound (31) was vacuum-deposited on a cleaned glass substrate with an ITO electrode to form a hole-injecting layer having a thickness of 30 nm. Then, Compound (32) having the following chemical structure was vapor-deposited thereon to form a light-emitting layer having a thickness of 40 nm. Further, Compound (9) was vacuum-deposited thereon to form an electron-injecting layer having a thickness of 20 nm. Then, an electrode having a thickness of 150 nm was formed thereon from an aluminum/lithium alloy having an aluminum/lithium mixing ratio of 100/3, to obtain an organic EL device. The hole-injecting layer, the light-emitting layer, the electron-injecting layer and the cathode were formed by deposition under a vacuum of $10^{-6}$ Torr at a substrate temperature of room temperature. The organic EL device showed a yellowish green light emission of 13,500 ($cd/m^2$) at a direct current voltage of 8 V.

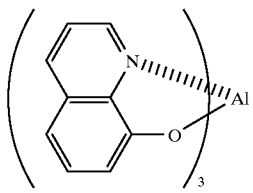

Example 23

Compound (31) was vacuum-deposited on a cleaned glass substrate with an ITO electrode to form a hole-injecting layer having a thickness of 30 nm. Then, Compound (33) having the following chemical structure was vapor-deposited thereon to form a light-emitting layer having a thickness of 40 nm. Further, Compound (9) was vacuum-deposited thereon to form an electron-injecting layer having a thickness of 20 nm. Then, an electrode having a thickness of 150 nm was formed thereon from an aluminum/lithium alloy having an aluminum/lithium mixing ratio of 100/3, to obtain an organic EL device. The hole-injecting layer, the light-emitting layer, the electron-injecting layer and the cathode were formed by deposition under a vacuum of $10^{-6}$ Torr at a substrate temperature of room temperature. The organic EL device showed a blue light emission of 12,000 ($cd/m^2$) at a direct current voltage of 8 V.

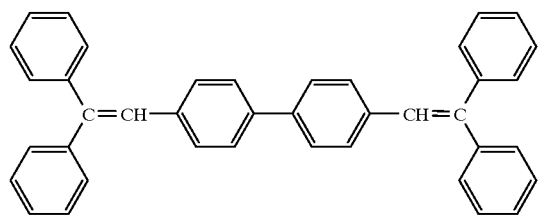

Example 24

Compound (31) was vacuum-deposited on a cleaned glass substrate with an ITO electrode to form a hole-injecting layer having a thickness of 30 nm. Then, a solution of poly(2,5-hexylthio-p-phenylenevinylene) having a number average molecular weight of 25,000 in chloroform was spin-coated on the hole-injecting layer to form a light-emitting layer having a thickness of 40 nm. Further, Compound (9) was vacuum-deposited thereon to form an electron-injecting layer having a thickness of 20 nm. Then, an electrode having a thickness of 150 nm was formed thereon from a magnesium/silver alloy having a magnesium/silver mixing ratio of 10/1, to obtain an organic EL device. The hole-injecting layer, the electron-injecting layer and the cathode were formed by deposition under a vacuum of $10^{-6}$ Torr at a substrate temperature of room temperature. The organic EL device showed a greenish yellow light emission of 10,500 ($cd/m^2$) at a direct current voltage of 8 V.

Example 25

Compound (31) was vacuum-deposited on a cleaned glass substrate with an ITO electrode to form a hole-injecting layer having a thickness of 30 nm. Then, Compound (30) was vapor-deposited thereon to form a light-emitting layer having a thickness of 40 nm. Further, Compound (7) was vacuum-deposited thereon to form an electron-injecting layer having a thickness of 20 nm. Then, an electrode having a thickness of 150 nm was formed thereon from an aluminum/lithium alloy having an aluminum/lithium mixing ratio of 100/3, to obtain an organic EL device. The hole-injecting layer, the light-emitting layer, the electron-injecting layer and the cathode were formed by deposition under a vacuum of $10^{-6}$ Torr at a substrate temperature of room temperature. The organic EL device showed a bluish green light emission of 15,000 ($cd/m^2$) at a direct current voltage of B V and a light emission efficiency of 2.35 (lm/W).

Comparative Example 1

An organic EL device was obtained in the same manner as in Example 21 except that Compound (7) for a light-emitting material was replaced with Compound (34) having the following chemical structure. The organic EL device was measured for a light emission brightness. The organic EL device showed a yellowish green light emission of 11,000 (cd/m²) at a direct current voltage of 8 V and a light emission efficiency of 0.81 (lm/W). It was found that the light emission was made from Compound (34).

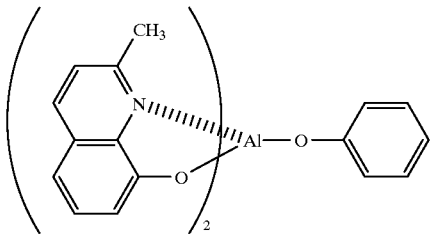

Comparative Examples 2–3

Organic EL devices were obtained in the same manner as in Example 25 except that Compound (7) for an electron-injecting layer was replaced with compounds shown in Table 3. The organic EL devices were measured for light emission brightness at a direct current voltage of 8 V.

TABLE 3

|  | Electron-injecting material | Brightness (cd/m²) | Light emission efficiency (lm/W) |
|---|---|---|---|
| Example 25 | Compound (7) | 12,000 | 2.35 |
| Comparative Example 2 | Compound (32) | 9,500 | 1.15 |
| Comparative Example 3 | Compound (34) | 6,500 | 0.80 |

The organic EL devices obtained in the above Examples, having the structure of at least 2 layers, showed a light emission color of from blue to bluish green, a light emission brightness of at least 5,000 cd/m² and high light emission efficiency. Further, when the organic EL devices obtained in the above Examples were allowed to continuously emit light at 3 mA/cm², all the organic EL devices emitted light having a brightness of at least ½ of the initial brightness for more than 10,000 hours. While the organic EL device obtained in Example 25 had a stable light emission brightness for more than 10,000 hours and showed almost no dark spots, while the organic EL devices obtained under the same conditions in Comparative Examples 2 and 3 showed light emission brightnesses which decreased to ½ or less of the initial brightness within 500 hours. Further, the organic EL devices obtained in Comparative Examples 2 and 3 showed many dark spots, and with the passage of time in measurement, the number of dark spots increased, and the sizes thereof increased. The reason therefor is assumed to be as follows. Compounds used in place of the compound of the present invention was poor in adhesion to the light-emitting layer and to the cathode and in formability, and the light-emitting layer and the cathode were greatly different in work function. The above results show that the use of the gallium complex of the present invention in the light-emitting layer or in a layer between the light-emitting layer and the cathode gives an organic EL device having a high light emission efficiency and an increased device life.

The organic EL device according to the present invention accomplishes improvements in light emission efficiency and brightness, and achieves an increased device life. There is therefore no limitation to be imposed on the light-emitting material, dopant, hole-injecting material, electron-injecting material, sensitizer, resin and electrode material which are used in combination of the gallium complex of the present invention, nor is the method of producing the device limited.

An organic EL device having a light-emitting layer formed of the gallium complex of the present invention or a layer formed of the gallium complex of the present invention between a light-emitting layer and a cathode exhibits a high light emission efficiency and an increased device life as compared with conventional organic EL devices. When the gallium complex of the present invention is used to form at least one layer of an organic EL device, the organic EL device exhibits a high light emission brightness, a high light emission efficiency and a long device life.

What is claimed is:

1. An organic electroluminescent (EL) device material of the general formula (1),

(1)

wherein each of $Q^1$ and $Q^2$ is independently a ligand of the general formula (2), and L is a substituted or unsubstituted alkyl group, a substituted or unsubstituted cycloalkyl group, a substituted or unsubstituted aryl group, a substituted or unsubstituted heterocyclic ring group, —$OR^1$ in which $R^1$ is a hydrogen atom, a substituted or unsubstituted alkyl group, a substituted or unsubstituted cycloalkyl group, a substituted or unsubstituted aryl group or a substituted or unsubstituted heterocyclic ring group, or —O—Ga—$Q^3(Q^4)$ in which $Q^3$ and $Q^4$ have the same meanings as those of $Q^1$ and $Q^2$, with the proviso that L is not a ligand of general formula (2),

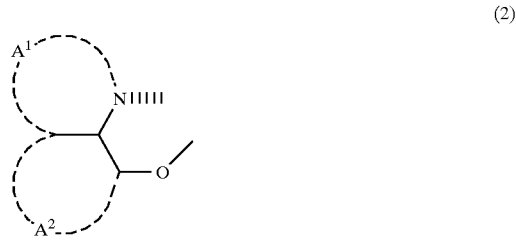

(2)

wherein $A^1$ and $A^2$ are substituted or unsubstituted six-membered aryl rings which are mutually fused to form a fused ring moiety.

2. A material according to claim 1, wherein L in the general formula (1) is —$OR^1$ in which $R^1$ is a hydrogen atom, a substituted or unsubstituted alkyl group, a substituted or unsubstituted cycloalkyl group, a substituted or unsubstituted aryl group or a substituted or unsubstituted heterocyclic ring group.

3. A material according to claim 2, wherein $Q^1$ or $Q^2$ in the general formula (1) is a ligand of the general formula (3),

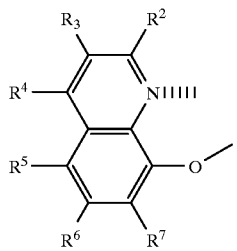

in which each of $R^2$ to $R^7$ is independently a hydrogen atom, a halogen atom, cyano, nitro, a substituted or unsubstituted alkyl group, a substituted or unsubstituted cycloalkyl group, a substituted or unsubstituted aryl group or a substituted or unsubstituted heterocyclic ring group.

4. A material according to claim 2, wherein $Q^1$ or $Q^2$ in the general formula (1) is a ligand of the formula (4),

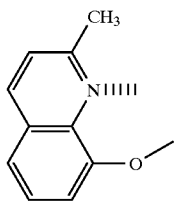

5. An organic EL device comprising a light-emitting layer or a plurality of thin organic compound layers including the light-emitting layer, the light-emitting layer or a plurality of the thin organic compound layers being sandwiched between an anode and a cathode, wherein the light-emitting layer or at least one of a plurality of the thin organic compound layers contains the organic EL device material of claim 1.

6. A device according to claim 5, wherein the light-emitting layer contains the organic EL device material of claim 1.

7. A device according to claim 5, wherein at least one of a plurality of the thin organic compound layers contains the organic EL device material of claim 1.

8. A device according to claim 5, wherein at least one of a plurality of the thin organic compound layers contains an arylamine derivative.

9. A material according to claim 1, having a structure selected from the group consisting of

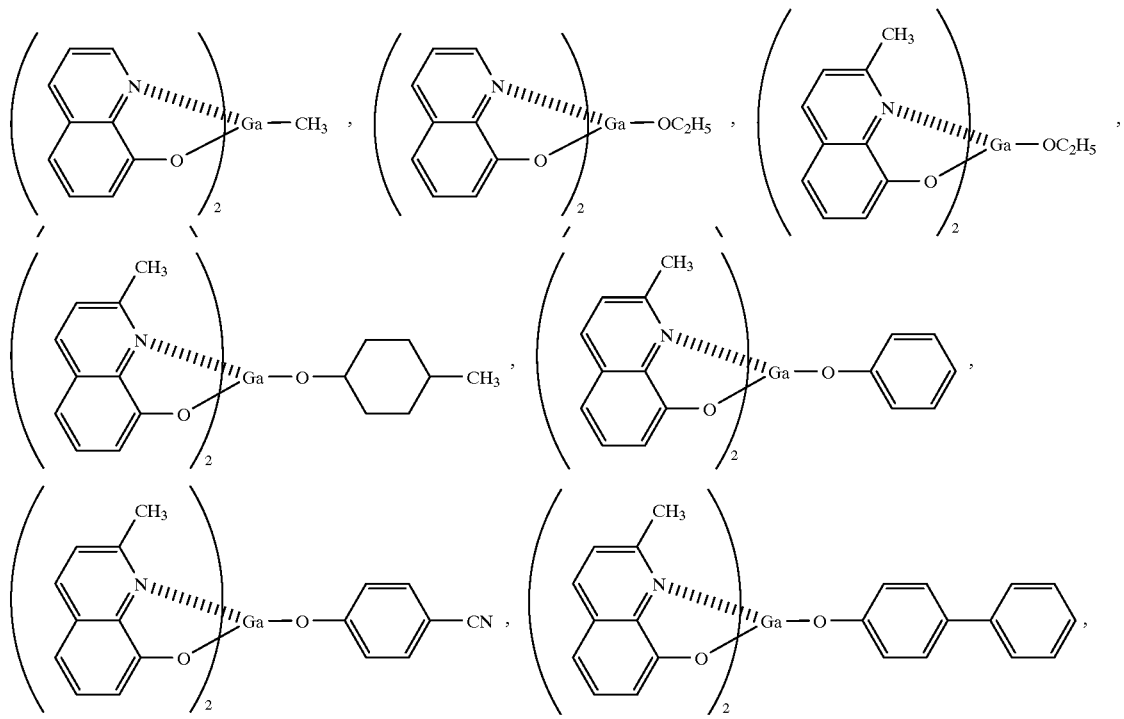

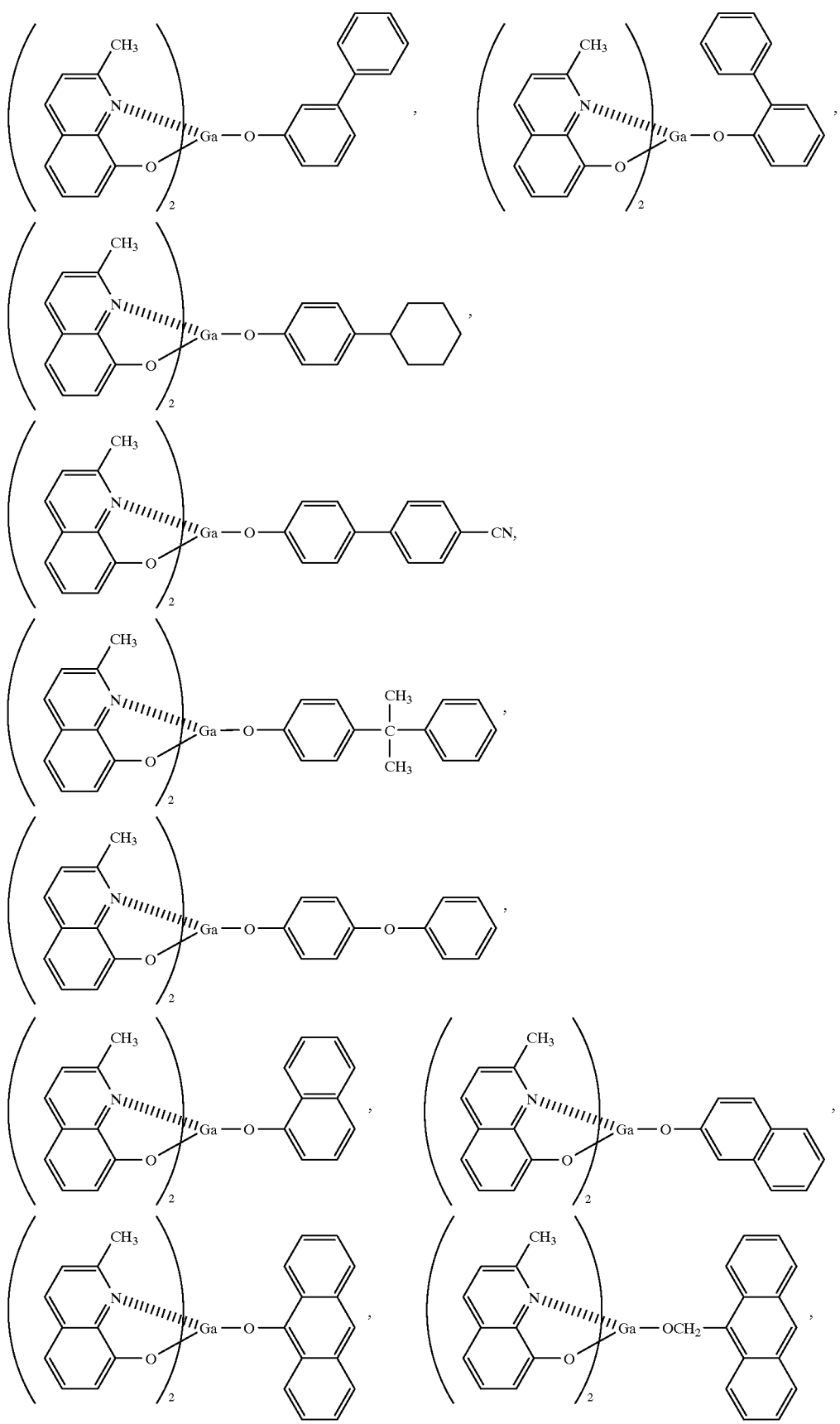

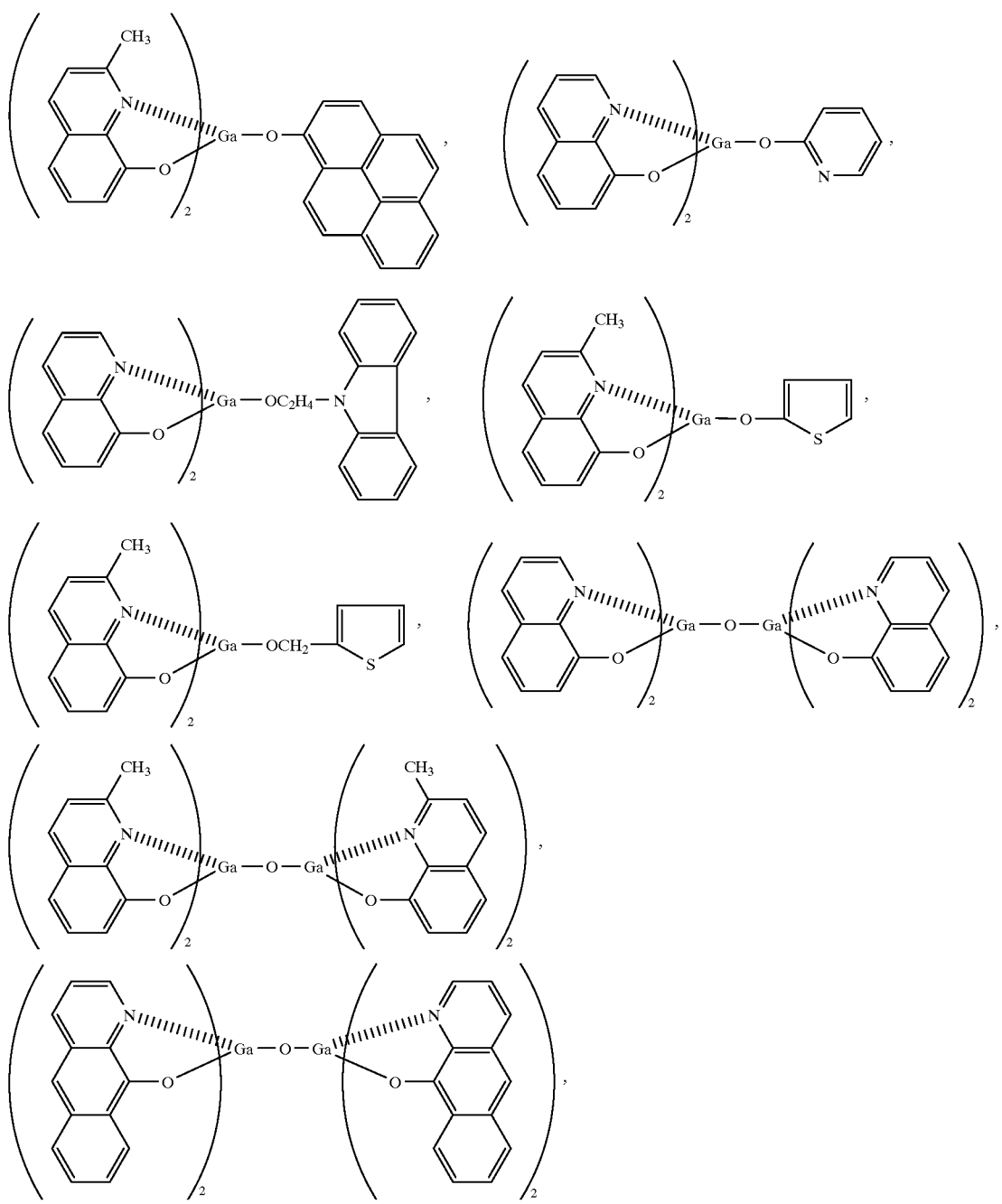
and
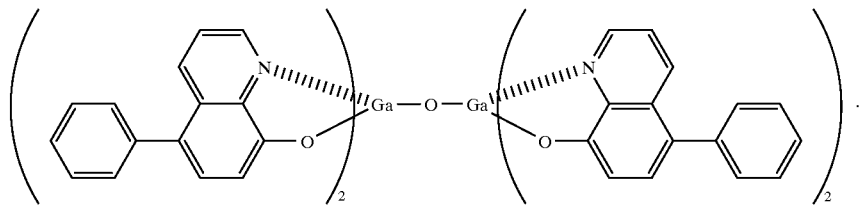

-continued
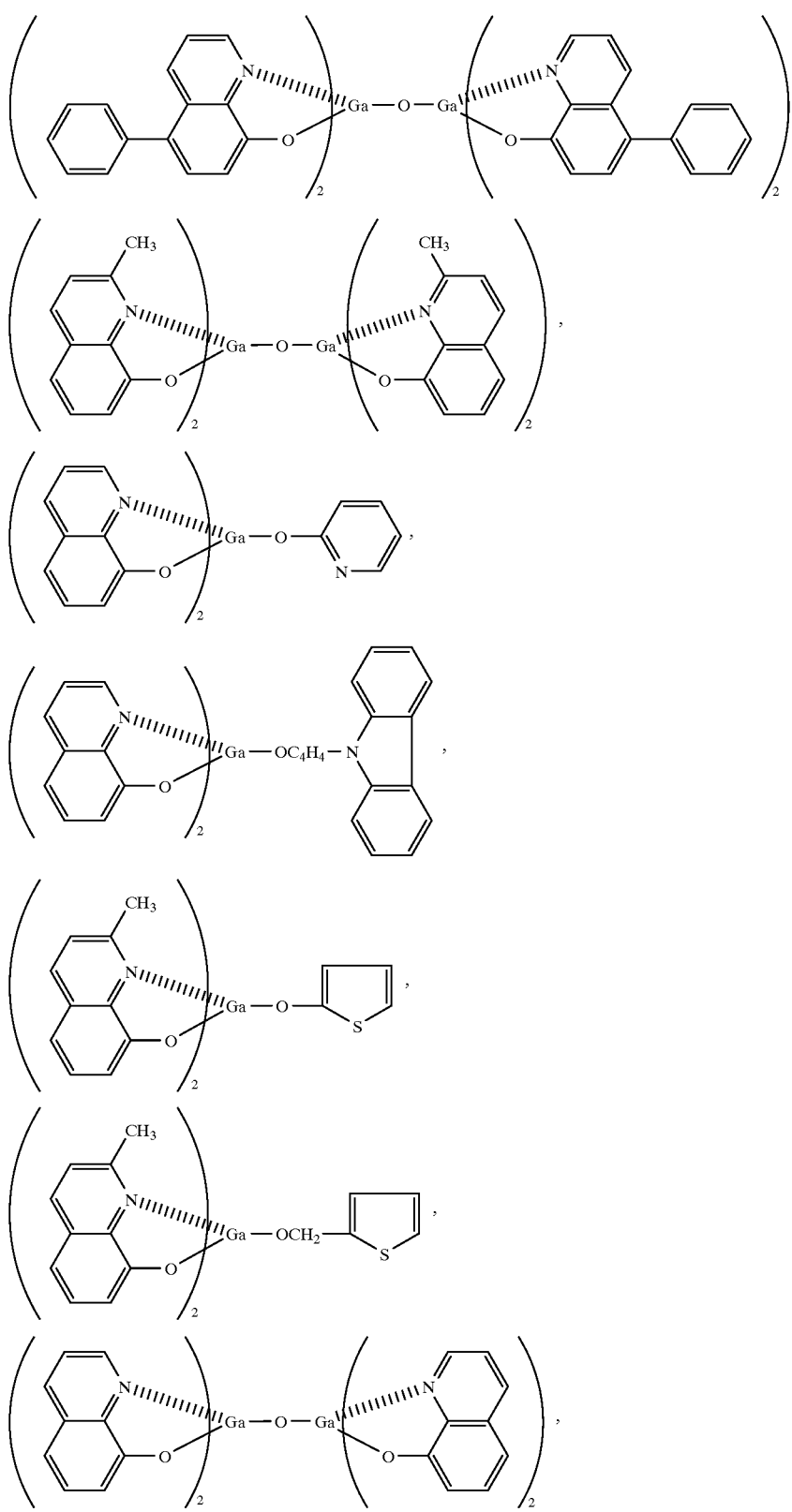

-continued
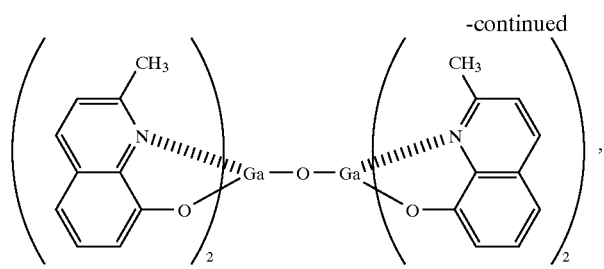
10. An electron-injecting material comprising the organic electroluminescent material of claim 1.
* * * * *

UNITED STATES PATENT AND TRADEMARK OFFICE
CERTIFICATE OF CORRECTION

PATENT NO. : 6,001,284
DATED : December 14, 1999
INVENTOR(S) : Toshio Enokida et al.

It is certified that error appears in the above-identified patent and that said Letters Patent is hereby corrected as shown below:

Column 1,
Line 51, change "lightemission" to -- light emission --.
Line 54, change "efficieny, and" to -- efficiency, and --.

Column 2,
Line 12, change "(2),1" to -- (2), --.

Column 3,
Line 2, change "six-membe red" to -- six-membered --.
Line 13, change "las" to -- as --.
Line 23, change "1, 1, 1, 13, 3, 3-hexafluoro-2-propoxy" to -- 1, 1, 1, 1, 3, 3, 3-hexafluoro-2-propoxy --.
Line 40, change "phenyicarbamoyl" to -- phenylcarbamoyl --.
Line 42, change "hudroxyl" to -- hydroxy --.
Line 43, change "phenahtryl" to -- phenanthryl --.
Line 53, change "ary" to -- aryl --.

Column 4,
Line 3, change "C.," to -- C, --.
Line 6, change "ligang" to -- ligand --.
Lines 65 and 66, change "galliumhydroxide, galliumoxide, galliumalkoxides" to -- gallium hydroxide, gallium oxide, gallium alkoxides --.
Line 67, change "triisopropxyallium" to -- triisopropoxygallium --.

Column 5,
Line 11, change "sulfolaneorwater" to -- sulfolane or water --.

Column 15,
Line 53, change "cojugated" to -- conjugated --.

Column 17,
Lines 14 and 15, change "inthelightemissionwavelengthregionofthedevice" to -- in the light emission wavelength region of the device --.

Column 18,
Line 40, change "ethanolwereplacedinaflaskandstirred. Further, asolution" to -- ethanol were placed in a flask and stirred. Further, a solution --.
Lines 47 and 48, change "for5hourstoprecipitateasolid" to -- for 5 hours to precipitate a solid --.

UNITED STATES PATENT AND TRADEMARK OFFICE
CERTIFICATE OF CORRECTION

PATENT NO. : 6,001,284
DATED : December 14, 1999
INVENTOR(S) : Toshio Enokida et al.

It is certified that error appears in the above-identified patent and that said Letters Patent is hereby corrected as shown below:

Column 19,
Line 12, change "Further, 5.5" to -- Further, 5.5 --.
Line 13, change "4-cyclohexylphenolwasadded" to -- 4-cyclohexylphenol was added --.

Column 20,
Line 9, change "Fig. 7" to -- Fig. 6 --.
To the right of the formula insert -- (29) --.

Column 22,
To the right of the formula insert -- (30) --.

Column 23,
To the right of the top formula insert (31) --.
To the right of the bottom formula insert -- (32) --.

Column 24,
To the right of the formula insert -- (33) --.

Column 25,
To the right of the formula insert -- (34) --.

Column 26,
Line 24, after "device" insert -- comprising at least a layer structure of anode/hole-injecting layer/light-emitting layer/cathode, wherein the hole-injecting layer contains a --.
Line 64, delete "A material" and insert therefor -- The EL device --.

Column 27,
Line 3, delete "A material" and insert -- The EL device --.
To the right of the top formula insert -- (3) --.
Line 26, delete "A material" and insert -- The EL device --.

UNITED STATES PATENT AND TRADEMARK OFFICE
CERTIFICATE OF CORRECTION

PATENT NO. : 6,001,284
DATED : December 14, 1999
INVENTOR(S) : Toshio Enokida et al.

It is certified that error appears in the above-identified patent and that said Letters Patent is hereby corrected as shown below:

<u>Column 28,</u>
To the right of the top formula insert -- (4) --.
Please delete lines 10-24 (i.e. cancel claims 5-7).
Line 25, change "8. A device according to claim 5" to -- 5. The EL device according to claim 1 --.
Line 28, change "9. A material" to -- 6. The El device --.
Line 28, delete "having" and insert -- wherein the material has --.

Delete columns 33-36 in its entirety (i.e. formulas and claim 10)

Signed and Sealed this

Thirteenth Day of November, 2001

Attest:

NICHOLAS P. GODICI
Attesting Officer     Acting Director of the United States Patent and Trademark Office